United States Patent
Watanabe et al.

(10) Patent No.: US 9,034,860 B2
(45) Date of Patent: May 19, 2015

(54) PHARMACEUTICAL COMPOSITION CONTAINING LOW-SUBSTITUTED HYDROXYPROPYL CELLULOSE

(75) Inventors: Tomoyuki Watanabe, Kanagawa (JP); Kazuko Maeda, Kanagawa (JP)

(73) Assignees: DAIICHI SANKYO COMPANY, LIMITED, Tokyo (JP); UBE INDUSTRIES, LTD., Ube-shi (JP)

( * ) Notice: Subject to any disclaimer, the term of this patent is extended or adjusted under 35 U.S.C. 154(b) by 455 days.

(21) Appl. No.: 12/312,973

(22) PCT Filed: Dec. 6, 2007

(86) PCT No.: PCT/JP2007/073552
§ 371 (c)(1),
(2), (4) Date: Jun. 2, 2009

(87) PCT Pub. No.: WO2008/072535
PCT Pub. Date: Jun. 19, 2008

(65) Prior Publication Data
US 2010/0093786 A1    Apr. 15, 2010

(30) Foreign Application Priority Data
Dec. 7, 2006  (JP) ................................. 2006-330375

(51) Int. Cl.
A61K 31/4365  (2006.01)
A61P 7/02  (2006.01)
A61K 9/20  (2006.01)

(52) U.S. Cl.
CPC ........... *A61K 31/4365* (2013.01); *A61K 9/2054* (2013.01)

(58) Field of Classification Search
CPC .......................... A61K 31/4365; A61K 9/2054
See application file for complete search history.

(56) References Cited

U.S. PATENT DOCUMENTS

| | | | |
|---|---|---|---|
| 4,931,286 A | 6/1990 | Johnson et al. | |
| 5,015,480 A | 5/1991 | Childers et al. | |
| 5,211,958 A | 5/1993 | Akkerboom et al. | |
| 5,288,726 A | 2/1994 | Koike et al. | |
| 5,618,799 A | 4/1997 | Inagi et al. | |
| 5,650,174 A | 7/1997 | Muhammad et al. | |
| 5,885,617 A | 3/1999 | Jordan | |
| 6,143,323 A | 11/2000 | Yabuki et al. | |
| 6,423,341 B1 | 7/2002 | Yamaguchi | |
| 6,693,115 B2 | 2/2004 | Asai et al. | |
| 6,740,339 B1 | 5/2004 | Ohkouchi et al. | |
| 2001/0031734 A1* | 10/2001 | Tanno et al. | |
| 2002/0035248 A1 | 3/2002 | Luhn | |
| 2003/0026832 A1 | 2/2003 | Labergerie et al. | |
| 2003/0130310 A1 | 7/2003 | Kubota et al. | |
| 2003/0134872 A1 | 7/2003 | Asai et al. | |
| 2003/0147951 A1 | 8/2003 | Yabuki et al. | |
| 2004/0024013 A1 | 2/2004 | Asai et al. | |
| 2005/0192245 A1 | 9/2005 | Asai et al. | |
| 2006/0127475 A1 | 6/2006 | Makino et al. | |
| 2007/0154543 A1 | 7/2007 | Hoshino et al. | |
| 2008/0176893 A1 | 7/2008 | Dziennik et al. | |
| 2009/0291138 A1 | 11/2009 | Watanabe et al. | |
| 2010/0004279 A1 | 1/2010 | Watanabe et al. | |
| 2010/0280064 A1 | 11/2010 | Watanabe et al. | |
| 2011/0201814 A1 | 8/2011 | Watanabe et al. | |

FOREIGN PATENT DOCUMENTS

| | | |
|---|---|---|
| CN | 1452624 A | 10/2003 |
| EP | 1 298 132 A1 | 4/2003 |
| EP | 1 350 511 A1 | 10/2003 |
| EP | 1 555 032 A1 | 7/2005 |
| EP | 1 614 417 A1 | 1/2006 |
| EP | 1 656 930 A1 | 5/2006 |
| EP | 1656930 A1 | 5/2006 |
| JP | 59-42325 A | 3/1984 |

(Continued)

OTHER PUBLICATIONS

Gissinger D. et al., "A Comparative Evaluation of the Properties of Some Tablet Disintegrants," *Drug Development and Industrial Pharmacy* New York, NY, US., vol. 6, No. 5, Jan. 1, 1980, pp. 511-536.
Guyot-Hermann A.M., "Tablet disintegration and disintegrating agents," *S.T.P. Pharma Sciences*, 1992, FR, vol. 2, No. 6, 1992, pp. 445-462.
Matsumura M. et al., "Development of an abdominal magnetic resonance (MR) contrast agent formulation with Oral Magentic Particles (OMP, Ferristene)," *Pharmaceutica ACTA Helvetiae* Dec. 1998, vol. 73, No. 4, Dec. 1998.
Sunada H. et al., "Preparation, evaluation and optimization of rapidly disintegrating tablets," *Powder Technology* Jan. 22, 2002 Elsevier, NL, vol. 122, No. 2-3, pp. 188-198.
Supplementary European Search Report dated Oct. 14, 2009 for European patent application EP 07 85 0168.

(Continued)

*Primary Examiner* — Savitha Rao
*Assistant Examiner* — Gregg Polansky
(74) *Attorney, Agent, or Firm* — Oblon, McClelland, Maier & Neustadt, L.L.P.

(57) ABSTRACT

Disclosed is a pharmaceutical composition containing a compound represented by the general formula (I) below or a pharmacologically acceptable salt thereof, while having improved dissolvability. Specifically disclosed is a pharmaceutical composition containing (A) a compound represented by the general formula (I) below or a pharmacologically acceptable salt thereof, and (B) a low-substituted hydroxypropyl cellulose.

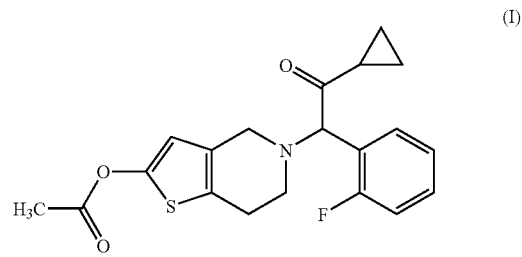

(I)

15 Claims, No Drawings

(56) References Cited

FOREIGN PATENT DOCUMENTS

| | | |
|---|---|---|
| JP | 1-175936 A | 7/1989 |
| JP | 2-211 A | 1/1990 |
| JP | 2-240024 A | 9/1990 |
| JP | 6-41139 A | 2/1994 |
| JP | 7-70506 A | 3/1995 |
| JP | 8-12582 A | 1/1996 |
| JP | 8-59512 A | 3/1996 |
| JP | 09-002953 A | 1/1997 |
| JP | 9-208458 A | 8/1997 |
| JP | 2003/73274 A | 8/1997 |
| JP | 10-194969 A | 7/1998 |
| JP | 10-310586 A | 11/1998 |
| JP | 2001-346600 A | 12/2001 |
| JP | 2002-145883 A | 5/2002 |
| JP | 2002-255814 A | 9/2002 |
| JP | 2003-160500 A | 6/2003 |
| JP | 2003-246735 | 9/2003 |
| JP | 2003-246735 A | 9/2003 |
| JP | 2004-51639 A | 2/2004 |
| JP | 2005-162619 A | 6/2005 |
| JP | 2006-206612 A | 8/2006 |
| WO | WO 97/31639 A1 | 9/1997 |
| WO | WO 2004/091600 A1 | 10/2004 |
| WO | WO 2004/098713 A2 | 11/2004 |
| WO | WO 2005/013964 A1 | 2/2005 |
| WO | WO 2006/135605 A2 | 12/2006 |
| WO | WO 2006/138317 A2 | 12/2006 |
| WO | WO 2007/020935 A1 | 2/2007 |
| WO | WO 2008/069262 A1 | 6/2008 |
| WO | WO 2008/072532 A1 | 6/2008 |
| WO | WO 2008/072533 A1 | 6/2008 |
| WO | WO 2008/072534 A1 | 6/2008 |

OTHER PUBLICATIONS

English-language International Preliminary Report on Patentability dated Jun. 10, 2009 and Written Opinion of the International Searching Authority, of International Application PCT/JP2007/073552 filed Dec. 6, 2007; Applicants: Daiichi Sankyo Company, Limited et al.
Barkley, Tablets & Capsules, Apr. 2006, pp. 1 to 5.
Jakubowski et al., "A multiple does stud of prasugrel (CS-747), a novel thienopyridine P2Y12 inhibitor, compared with clopidogrel in healthy humans," *British Journal of Clinical Pharmacology*(2006), 63:4, pp. 421 to 430.
Remmington's Pharmaceutical Sciences, 1985, Chapter 90, pp. 1603-1632.
"Emerging Drug List Prasugrel for Patients With Acute Coronary Syndrome Undergoing Balloon Angioplasty" Canadian Coordinating Office for Health Technology Assessment No. 63, Jun. 2005, pp. 1-5 of 5.
L.S.C. Wan et al., "Citric acid as a plasticizer for spray-dried microcapsules," *Journal of Microencapsulation*, (1993), vol. 10, No. 1, pp. 11 to 23.
Heidarian, M. et al., "Influence of water-cellulose binding energy on stability of acetylsalicylic acid," *International Journal of Pharmaceutics*, Elsevier BV, NL. vol. 323, No. 1-2, Oct. 12, 2006, pp. 139 to 145.

Landin, M. et al., "Influence of microcrystalline cellulose source and batch variation on the tabletting behaviour and stability of prednisone formulations," *International Journal of Pharmaceutics*, Elsevier BV, NL., vol. 91, No. 2-3, Apr. 26, 1993, pp. 143 to 149.
Stewart, P.J. et al., "Understanding agglomeration of indomethacin during the dissolution of micronised indomethacin mixtures through dissolution nd de-agglomeration modeling approaches," *Europe Journal of Pharmaceutics and Biopharmaceutics*, Elsevier Science Publishers B.V., Amsterdam, NL, vol. 59, No. 2, Feb. 1, 2005, pp. 315 to 323.
De Villiers, Melgardt M., "Description of the kinetics of the deagglomeration of drug particle agglomerates during powder mixing," *International Journal of Pharmaceutics*, (Amsterdam), vol. 151, No. 1, 1997, pp. 1 to 6.
Kokubo, Hiroyasu et al., "Effect of Process Variables on the Properties and Binder Distribution of Granules Prepared by a High-Speed Mixer," *Chem. Pharm. Bull.*, (Tokyo), vol. 44, No. 8, (1996), pp. 1546 to 1549.
Fanelli, M. et al., "Prediction of the dispersion of particle clusters in the nano-scale—Part II, unsteady shearing responses," *Chemical Engineering Science*, (Oxford, GB), vol. 61, No. 15, Aug. 1, 2006, pp. 4944-4956.
Sakr, M. et al., "Influence of Mixers on the Characteristics of Triamterene/Hydrochlorothiazide Directly Compressed Tablets," *Pharmazeutische Industrie*, DE, vol. 55, No. 7, (1993), pp. 705 to 708.
Larhrib Hassan et al., "The use of different grades of lactose as a carrier for aerosolised salbutamol sulphate," *International Journal of Pharmaceutics* (Amsterdam), vol. 191, No. 1, Nov. 25, 1999, pp. 1 to 14.
Flament Marie-Pierre et al., "The influence of carrier roughness on adhesion, content uniformity and the in vitro deposition of terbutaline sulphate from dry powder inhalers," *International Journal of Pharmaceutics* (Kidlington), vol. 275,, No. 1-2, May 4, 2004, pp. 201 to 209.
Schiavone Helena et al., "Evaluation of SCF-engineered particle-based lactose blends in passive dry powder inhalers," *International Journal of Pharmaceutics* (Kidlington), vol. 281, No. 1-2, Aug. 20, 2004, pp. 55 to 66.
He, M.M. et al., "Drug Content Uniformity of Binary Powder Blends in the Rotary Fluid Bed Granulator," *Pharmazeutische Industrie*, DE, (1995), vol. 57, No. 11, pp. 945 to 949.
Joshi, B.V. et al., "Compatibility Studies Between Carbamazepine and Tablet Excipients Using Thermal and Non-thermal Methods," *Drug Development and Industrial Pharmacy*, Jul. 2002, vol. 28, No. 6, pp. 687 to 694.
Notification of Reexaminaion dated Apr. 13, 2013 which issued in Chinese application 200780044970.X (along with an English-language translation of said Notification of Reexamination).
Office Action issued Feb. 19, 2014 in Chinese Patent Application No. 200780044970.X (with English language translation).
Ying Zhu, et al., "Development and mathematical simulation of theophylline pulsatile release tablets", Drug Development and Industrial Pharmacy, vol. 31, 2005, pp. 1009-1017.
E. Sallam, et al., "Evaluation of fast disintegrants in terfenadine tablets containing a gas-evolving disintegrant", Drug Development and Industrial Pharmacy, vol. 24, No. 6, 1998, pp. 501-507.

* cited by examiner

PHARMACEUTICAL COMPOSITION CONTAINING LOW-SUBSTITUTED HYDROXYPROPYL CELLULOSE

This application is a U.S. National Phase Application under 35 USC 371 of International Application PCT/JP2007/073552, filed Dec. 6, 2007, which is incorporated herein in its entirety by this reference.

TECHNICAL FIELD

The present invention relates to a pharmaceutical composition containing
(A) a compound represented by the following general formula (I):

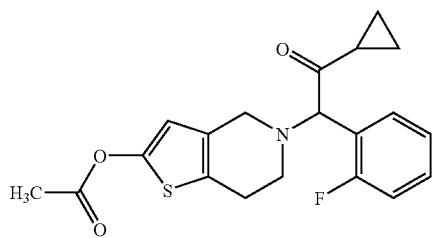

or a pharmacologically acceptable salt thereof; and
(B) a low-substituted hydroxypropyl cellulose.

BACKGROUND ART

The compound represented by the aforementioned general formula (I) or the pharmacologically acceptable salt thereof is known as a compound having platelet aggregation inhibition activity (Patent Document 1 or 2).

Patent Documents 2, 3, 4 and 5 exemplify various kinds of additives that may be used in preparations containing the compound represented by the aforementioned general formula (I) or a pharmacologically acceptable salt thereof, and there is a line which mentions low-substituted hydroxypropyl cellulose as one such additive.

However, in all of these Patent Documents, the low-substituted hydroxypropyl cellulose is merely exemplified as one example of various additives, and is not used specifically in a preparation example. Further, the aforementioned Patent Documents neither describe nor teach that the dissolvability of the pharmaceutical composition containing the compound represented by the aforementioned general formula (I) or the pharmacologically acceptable salt thereof can be improved by including a low-substituted hydroxypropyl cellulose.

[Patent Document 1] Japanese Patent Application (Kokai) No. Hei 6-41139
[Patent Document 2] Japanese Patent Application (Kokai) No. 2002-145883
[Patent Document 3] Japanese Patent Application (Kokai) No. Hei 10-310586
[Patent Document 4] Japanese Patent Application (Kokai) No. 2003-246735
[Patent Document 5] Japanese Patent Application (Kokai) No. 2004-51639

DISCLOSURE OF THE INVENTION

Problems to be Solved by the Invention

An object of the present invention is to provide a pharmaceutical composition having improved dissolvability which contains the compound represented by the aforementioned general formula (I) or a pharmacologically acceptable salt thereof.

Means for Solving the Problems

As a result of conducting extensive studies to solve the aforementioned problems, the inventors of the present invention found that the dissolvability of a pharmaceutical composition containing the compound represented by the aforementioned general formula (I) or a pharmacologically acceptable salt thereof can be improved by including a low-substituted hydroxypropyl cellulose, thereby leading to completion of the present invention.

The present invention provides a pharmaceutical composition containing (A) the compound represented by the aforementioned general formula (I) or a pharmacologically acceptable salt thereof, and (B) a low-substituted hydroxypropyl cellulose (particularly a composition for prophylaxis or treatment of thrombosis or embolism), use of the compound represented by the aforementioned general formula (I) or a pharmacologically acceptable salt thereof for the production of the pharmaceutical composition (particularly a pharmaceutical composition for prophylaxis or treatment of thrombosis or embolism), and a prophylaxis or treatment strategy for a disease (particularly thrombosis or embolism) in which the pharmaceutical composition containing an effective amount of the compound represented by the aforementioned general formula (I) or a pharmacologically acceptable salt thereof is administered to a warm-blooded animal (particularly a human).

That is, the present invention is:
(1) a pharmaceutical composition comprising:
(A) a compound represented by the following general formula (I):

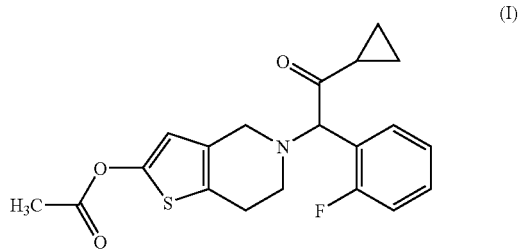

or a pharmacologically acceptable salt thereof; and
(B) a low-substituted hydroxypropyl cellulose, preferably,
(2) the pharmaceutical composition according to (1), wherein the amount of the low-substituted hydroxypropyl cellulose formulated is 2.5 to 40.0% by weight with respect to the total amount of the pharmaceutical composition,
(3) the pharmaceutical composition according to (1), wherein the amount of the low-substituted hydroxypropyl cellulose formulated is 5.0 to 40.0% by weight with respect to the total amount of the pharmaceutical composition,
(4) the pharmaceutical composition according to (1), wherein the amount of the low-substituted hydroxypropyl cellulose formulated is 10.0 to 30.0% by weight with respect to the total amount of the pharmaceutical composition,
(5) the pharmaceutical composition according to any one of (1) to (4), wherein the compound represented by the general formula (I) or the pharmacologically acceptable salt thereof is a compound represented by the following formula (Ia):

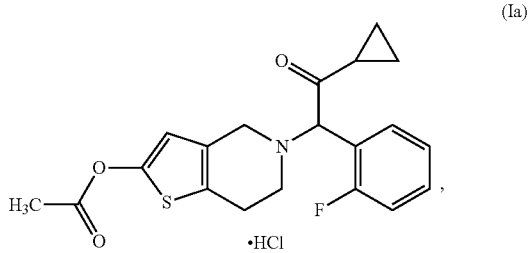

(6) the pharmaceutical composition according to any one of (1) to (5), characterized in that it is formed by a method comprising a step of formulating by a direct compression method, (7) the pharmaceutical composition according to any one of (1) to (6), wherein the pharmaceutical composition is in the form of powders, fine granules, granules, capsules or tablets, or (8) the pharmaceutical composition according to any one of (1) to (6), wherein the pharmaceutical composition is in the form of tablets.

Effect of the Invention

According to the present invention, a pharmaceutical composition containing the compound represented by the aforementioned formula (I) or a pharmacologically acceptable salt thereof which has improved dissolvability can be provided.

The pharmaceutical composition of the present invention is, for example, useful for the treatment and/or prophylaxis of thrombosis or embolism (preferably thrombosis) and the like (preferably is a drug for the treatment and/or prophylaxis of thrombosis).

BEST MODE FOR CARRYING OUT THE INVENTION

The compound represented by the following general formula (I):

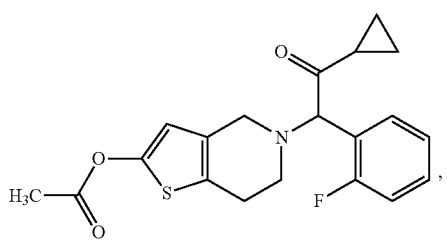

that is, 2-acetoxy-5-(α-cyclopropylcarbonyl-2-fluorobenzyl)-4,5,6,7-tetrahydrothieno[3,2-c]pyridine, or a pharmacologically acceptable salt thereof, which is the active ingredient of the pharmaceutical composition of the present invention, is disclosed in Japanese Patent Application (Kokai) No. Hei 6-41139 or Japanese Patent Application (Kokai) No. 2002-145883, and can be prepared accordingly.

As the "pharmacologically acceptable salt thereof" of the present invention, there may be mentioned for example, hydrohalides such as hydrofluoride, hydrochloride, hydrobromide or hydroiodide; inorganic acid salts such as nitrate, perchloric acid salt, sulfate or phosphate; lower-alkyl sulfonic acid salts such as methanesulfonate, trifluoromethanesulfonate or ethanesulfonate; aryl sulfonic acid salts such as benzenesulfonate or p-toluenesulfonate; organic acid salts such as acetate, malate, fumarate, succinate, citrate, ascorbate, tartrate, oxalate or maleate; or an amino acid salts such as glycine salt, lysine salt, arginine salt, ornithine salt, glutamic acid salt or aspartic acid salt, preferably hydrohalides or organic acid salts, more preferably hydrochloride or maleate, and most preferably hydrochloride.

The pharmaceutical composition of the present invention contains a low-substituted hydroxypropyl cellulose, and may further contain additives such as appropriate pharmacologically acceptable fillers, lubricants, binders, emulsifiers, stabilizers, corrigents and/or diluents.

As the "fillers" used, there may be mentioned for example, organic fillers including sugar derivatives such as lactose, sucrose, glucose, mannitol or sorbitol; starch derivatives such as corn starch, potato starch, α-starch or dextrin; cellulose derivatives such as crystalline cellulose; gum Arabic; dextran; or pullulan: or inorganic fillers including silicate derivatives such as light anhydrous silicic acid, synthetic aluminum silicate, calcium silicate or magnesium metasilicate aluminate; phosphates such as calcium hydrogen phosphate; carbonates such as calcium carbonate; or sulfates such as calcium sulfate. Of these, one or more fillers selected from sugar derivatives and cellulose derivatives are preferably used, one or more fillers selected from lactose, mannitol and crystalline cellulose are more preferably used, and lactose and/or crystalline cellulose are most preferably used.

As the "lubricants" used, there may be mentioned for example, stearic acid; stearic acid metal salts such as calcium stearate or magnesium stearate; talc; colloidal silica; waxes such as beeswax or spermaceti; boric acid; adipic acid; sulfates such as sodium sulfate; glycol; fumaric acid; sodium stearyl fumarate; sucrose fatty acid esters; sodium benzoate; D,L-leucine; lauryl sulfates such as sodium lauryl sulfate or magnesium lauryl sulfate; silicates such as silicic anhydride or silicate hydrate; or the aforementioned starch derivatives. Of these, stearic acid metal salts are preferably used.

As the "binders" used, there may be mentioned for example, hydroxypropyl cellulose, hydroxypropylmethyl cellulose, polyvinylpyrrolidone, polyethylene glycol, or the same compounds as the aforementioned fillers. Of these, hydroxypropyl cellulose or hydroxypropylmethyl cellulose is preferably used.

As the "emulsifiers" used, there may be mentioned for example, colloidal clays such as bentonite or beegum; metal hydroxides such as magnesium hydroxide or aluminum hydroxide; anionic surfactants such as sodium lauryl sulfate or calcium stearate; cationic surfactants such as benzalkonium chloride; or nonionic surfactants such as polyoxyethylene alkyl ether, polyoxyethylene sorbitan fatty acid ester or sucrose fatty acid ester.

As the "stabilizers" used, there may be mentioned for example, para-oxybenzoic acid esters such as methyl paraben or propyl paraben; alcohols such as chlorobutanol, benzyl alcohol or phenyl ethyl alcohol; benzalkonium chloride; phenols such as phenol or cresol; thimerosal; dehydroacetic acid; or sorbic acid.

As the "corrigents" used, there may be mentioned for example, sweeteners such as sodium saccharin or aspartame; acidulants such as citric acid, malic acid or tartaric acid; or flavorings such as menthol, lemon or orange.

Although there is no particular limitation as regards the amount of the compound represented by the aforementioned general formula (I) or a pharmacologically acceptable salt thereof formulated in the entirety of the pharmaceutical composition, it is preferable to formulate 1.0 to 30.0% by weight (preferably 1.3 to 20.0% by weight) with respect to the total weight of the pharmaceutical composition.

Although there is no particular limitation as regards the amount of additives formulated in the entirety of the pharmaceutical composition, it is preferable to formulate 2.5 to 40.0% by weight (preferably 5.0 to 40.0% by weight, and more preferably 10.0 to 30.0% by weight) of the low-substituted hydroxypropyl cellulose, 10.0 to 93.5% by weight (preferably 44.0 to 90.0% by weight) of fillers, 0.5 to 5.0% by weight (preferably 0.5 to 3.0% by weight) of lubricants, and 0.0 to 15.0% by weight (preferably 2.5 to 10.0% by weight) of binders, with respect to the total weight of the pharmaceutical composition.

The pharmaceutical composition of the present invention is preferably in the form of a solid preparation, and there may be mentioned for example, tablets (including sublingual tablets and tablets that disintegrate in the mouth), capsules (including soft capsules and microcapsules), granules, fine granules, powders, pills, chewables or troches. Preferably, it is in the form of powders, fine granules, granules, capsules or tablets, and most preferably tablets.

As regards production methods for the preparation of the present invention, there may be used a general method described in publications such as "Powder Technology and Pharmaceutical Process (D. Chulia et al., Elservier Science Pub Co (Dec. 1, 1993))". In particular, a dry method is preferable.

The dry method of the present invention includes a direct compression method and a dry granulation method, and a direct compression method is preferable.

The "direct compression method" is a method in which raw material powders are directly subjected to compression-molding to produce a preparation.

The "dry granulation method" is a method in which a preparation is produced using granules prepared by crushing and dividing by an appropriate method a compression-molded slug or sheet of raw material powders. These methods are described in publications such as "The Theory and Practice of Industrial Pharmacy (Third Edition) (Leon Lachman et al.: LEA & FEBIGER 1986)" and "Pharmaceutical Dosage Forms: Tablets volume 1 (Second Edition) (Herbert A. Lieberman et al.: MARCEL DEKKER INC. 1989)".

Granulation used here means an operation of forming granules having an almost uniform shape and size from a raw material in the form of powders, mass, solution, or molten liquid, and examples include granulation for forming a final product such as granules, powders or fine granules, and granulation for forming an intermediate product for the production of a tablet or a capsule.

The compression-molding process is a process in which a mass product of raw material powder is formed by applying pressure to the raw material powder using mechanical force, and examples of apparatuses used include rotary tableting machines (manufactured by Kikusui Seisakusho Ltd., Hata Iron Works Co., Ltd., Sugawara Seiki Co., Ltd. and the like), and dry granulators such as a roller compactor, a roll granulator and a Chilsonator (manufactured by Freund Corporation, Turbo Kogyo Co., Ltd., Kurimoto, Ltd., Matsubo Corporation, Nippon Granulator Co., Ltd., Fuji Paudal Co., Ltd. and the like).

The crushing and dividing process is a process in which the mass product formed in the compression-molding process is crushed by means of a knife or cutter into an appropriate size, and examples of apparatuses used include mills and particle size selectors such as a power mill, Fitzmill, Fiore, and Co-mill (manufactured by Fuji Paudal Co., Ltd., Tokuju Corporation, Powrex Corporation and the like).

The thus obtained granulated product is subjected to particle size regulation so as to have a desired particle diameter, and then a preparation in the form of powders, fine granules or granules is produced. These preparations can also be produced as capsules by packing them in a capsule, or can be produced as tablets by further adding disintegrants and/or lubricants if necessary and subjecting them to compression-molding by a tableting machine or the like. The operation of mixing and granulation are both widely used in the field of formulation techniques, and those skilled in the art can carry them out appropriately. In addition, tablets may be provided with at least one layer of a film-coating.

Coating is conducted by using a film-coating machine for example, and as the film coating base agent, there may be mentioned for example, sugar coating base agents, water-soluble film coating base agents, enteric film coating base agents or sustained release film coating base agents.

As the sugar coating base agents, saccharose is used, and one or more selected from talc, precipitated calcium carbonate, calcium phosphate, calcium sulfate, gelatin, gum Arabic, polyvinylpyrrolidone and pullulan can be used in combination.

As the water-soluble film coating base agents, there may be mentioned for example, cellulose derivatives such as hydroxypropyl cellulose, hydroxypropylmethyl cellulose, hydroxyethyl cellulose, methyl hydroxyethyl cellulose and sodium carboxymethyl cellulose; synthetic polymers such as polyvinyl acetal diethyl aminoacetate, aminoalkyl methacrylate copolymer and polyvinylpyrrolidone; and polysaccharides such as pullulan.

As the enteric film coating base agents, there may be mentioned for example, cellulose derivatives such as hydroxypropylmethyl cellulose phthalate, hydroxypropylmethyl cellulose acetate succinate, carboxymethylethyl cellulose or cellulose acetate phthalate; acrylic acid derivatives such as (meth)acrylic acid copolymer L, (meth)acrylic acid copolymer LD or (meth)acrylic acid copolymer S; or natural substances such as shellac.

As the sustained release film coating base agents, there may be mentioned for example, cellulose derivatives such as ethyl cellulose; or acrylic acid derivatives such as aminoalkyl methacrylate copolymer RS or ethyl acrylate-methyl methacrylate copolymer emulsion.

The aforementioned coating base agents may be used by combining two or more of them in an appropriate ratio. In addition, the coating base agents may, if necessary, further include additives such as appropriate pharmacologically acceptable plasticizers, fillers, lubricants, masking agents, colorants and/or antiseptics.

The plasticizers which may be used in the present invention are not particularly limited, and a person skilled in the art can select them appropriately. As for such plasticizers, there may be mentioned for example, propylene glycol, polyethylene glycol, polypropylene glycol, glycerin and sorbitol, glycerin triacetate, diethyl phthalate and triethyl citrate, lauric acid, sucrose, dextrose, sorbitol, triacetin, acetyl triethyl citrate, triethyl citrate, tributyl citrate or acetyl tributyl citrate.

As the masking agents which may be used in the present invention, there may be mentioned for example, titanium oxide.

As the colorants which may be used in the present invention, there may be mentioned for example, titanium oxide, iron oxide, red ferric oxide, yellow ferric oxide or yellow No. 5 aluminum lake talc.

As the antiseptics which may be used in the present invention, there may be mentioned for example, paraben.

The dosage amount of the compound represented by the aforementioned general formula (I) or a pharmacologically acceptable salt thereof, which is an active ingredient of the pharmaceutical composition of the present invention, may vary depending on various conditions such as the activity of the drug, symptoms, age or body weight of a patient. The daily dosage amount for an adult human has a lower limit of 0.01 mg (preferably 1 mg) and an upper limit of 200 mg (preferably 100 mg) in the case of oral administration.

EXAMPLES

The present invention will be described in more detail with reference to the Examples and Test Examples; however, the present invention shall not be limited to these.

Here, "Compound A" used in the Examples is the compound represented by the following formula (Ia):

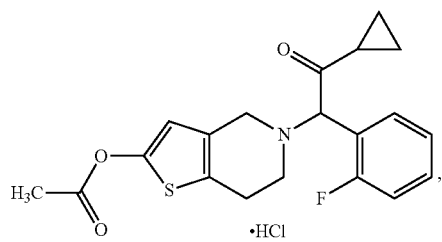

(Ia)

and can be prepared in accordance with the method disclosed in Japanese Patent Application (Kokai) No. 2002-145883.

Example 1

Compound A (32.9 g), low-substituted hydroxypropyl cellulose (24.0 g), hydroxypropyl cellulose (12.0 g) and lactose (168.7 g) were mixed using a high intensity mixer for 3 minutes, followed by addition of magnesium stearate (2.4 g), and the mixture was mixed again using the high intensity mixer to give a mixed powder.

The mixed powder obtained was compressed using a rotary type tableting machine with a tableting pressure of 5.9 kN so that the tablet mass became approximately 80 mg. Dissolution testing and disintegration testing were conducted on the obtained tablet. Test results are shown in Tables 1 and 2 respectively.

Example 2

Compound A (32.9 g), low-substituted hydroxypropyl cellulose (48.0 g), hydroxypropyl cellulose (12.0 g) and lactose (144.7 g) were mixed using a high intensity mixer for 3 minutes, followed by addition of magnesium stearate (2.4 g), and the mixture was mixed again using the high intensity mixer to give a mixed powder.

The mixed powder obtained was compressed using a rotary type tableting machine with a tableting pressure of 5.9 kN so that the tablet mass became approximately 80 mg. Dissolution testing and disintegration testing were conducted on the obtained tablet. Test results are shown in Tables 1 and 2 respectively.

Comparative Example 1

Compound A (32.9 g), carboxymethyl cellulose calcium (24.0 g), hydroxypropyl cellulose (12.0 g) and lactose (144.7 g) were mixed using a high intensity mixer for 3 minutes, followed by addition of magnesium stearate (2.4 g), and the mixture was mixed again using the high intensity mixer to give a mixed powder.

The mixed powder obtained was compressed using a rotary type tableting machine with a tableting pressure of 5.9 kN so that the tablet mass becomes approximately 80 mg. Dissolution testing and disintegration testing were conducted on the obtained tablet. Test results are shown in Tables 1 and 2 respectively.

Comparative Example 2

Compound A (32.9 g), hydroxypropyl cellulose (12.0 g) and lactose (192.7 g) were mixed using a high intensity mixer for 3 minutes, followed by addition of magnesium stearate (2.4 g), and the mixture was mixed again using the high intensity mixer to give a mixed powder.

The mixed powder obtained was compressed using a rotary type tableting machine with a tableting pressure of 5.9 kN so that the tablet mass became approximately 80 mg. Dissolution testing and disintegration testing were conducted on the obtained tablet. The results are shown in Tables 1 and 2 respectively.

Test Example 1

(1) Dissolution Test

Testing was conducted in accordance with the Dissolution Test (Method 2) described in the 14$^{th}$ Revised Edition of the Japanese Pharmacopoeia, using 900 mL of McIlvaine buffer (pH 4.0) as a test liquid at 50 revolutions per minute. A sample was individually taken from the test liquid after 5 minutes, 10 minutes, 15 minutes, and 30 minutes from the start of the test, and the dissolution rate of Compound A was measured by absorption spectrometry. (Dissolution tester manufactured by Toyama Sangyo Co., Ltd.; spectrophotometer manufactured by Shimadzu Corporation.) The testing was conducted on 6 tablets, and the average value of the dissolution rate was calculated. Test results are shown in Table 1.

(2) Disintegration Test

Testing was conducted in accordance with the Disintegration Test described in the 14$^{th}$ Revised Edition of the Japanese Pharmacopoeia, using water as a test liquid. The testing was conducted on 6 tablets, and the average value of the disintegration time was calculated. Test results are shown in Table 2.

TABLE 1

| Dissolution Time (min) | Example 1 Dissolution rate (%) | Example 2 Dissolution rate (%) | Comparative Example 1 Dissolution rate (%) | Comparative Example 2 Dissolution rate (%) |
|---|---|---|---|---|
| 5 | 73 | 78 | 44 | 11 |
| 10 | 76 | 85 | 51 | 16 |
| 15 | 78 | 88 | 55 | 22 |
| 30 | 81 | 91 | 61 | 59 |

TABLE 2

|  | Example 1 | Example 2 | Comparative Example 1 | Comparative Example 2 |
|---|---|---|---|---|
| Disintegration Time (min) | 1 | 1 | 1 | 9 |

From Table 1 and Table 2, it is obvious that the preparations containing the low-substituted hydroxypropyl cellulose (Examples 1 and 2) are superior in disintegration time and dissolvability, compared with the preparation which does not contain the low-substituted hydroxypropyl cellulose (Comparative Example 2).

In addition, carboxymethyl cellulose calcium, which is added in place of the low-substituted hydroxypropyl cellulose in Comparative Example 1, is an additive ingredient mentioned in one line of Japanese Patent Application (Kokai) No. Hei 10-310586, Japanese Patent Application (Kokai) No. 2002-145883 and Japanese Patent Application (Kokai) No. 2003-246735 as being one of the cellulose derivatives that can be used as an additive ingredient in similar manner to the low-substituted hydroxypropyl cellulose. When compared with Comparative Example 1, it is obvious that Examples 1 and 2 have significant dissolvability.

INDUSTRIAL APPLICABILITY

According to the present invention, a pharmaceutical composition having improved dissolvability, which contains the compound represented by the aforementioned general formula (I) or a pharmacologically acceptable salt thereof, and a low-substituted hydroxypropyl cellulose, can be obtained.

The invention claimed is:

1. A pharmaceutical composition comprising:
a compound represented by formula (I):

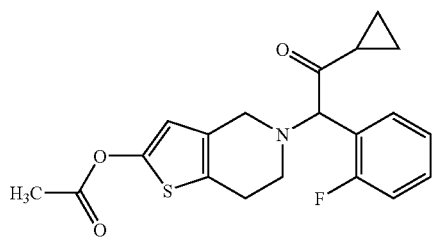

(I)

or a pharmacologically acceptable salt thereof;
a low-substituted hydroxypropyl cellulose;
hydroxypropyl cellulose;
lactose; and
magnesium stearate,
wherein the amount of the low-substituted hydroxypropyl cellulose is present in an amount of 10.0 to 30.0% by weight, hydroxypropyl cellulose is present in an amount of 2.5 to 10.0% by weight and magnesium stearate is present in an amount of 0.5 to 3.0% by weight with respect to a total amount of the pharmaceutical composition.

2. The pharmaceutical composition according to claim 1, wherein the compound represented by the formula (I) or the pharmacologically acceptable salt thereof is a compound represented by formula (Ia):

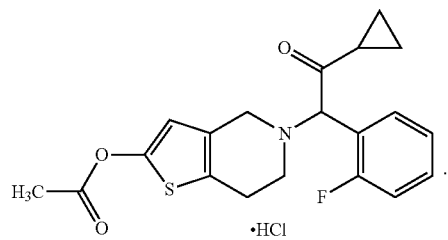

(Ia)

3. The pharmaceutical composition according to claim 2, wherein the composition is formed by a method comprising formulating by a direct compression method.

4. The pharmaceutical composition according to claim 1, wherein the composition is formed by a method comprising formulating by a direct compression method.

5. The pharmaceutical composition according to claim 1, wherein hydroxypropyl cellulose is present in an amount of 5.0 to 10.0% by weight with respect to the total amount of the pharmaceutical composition.

6. The pharmaceutical composition according to claim 2, wherein hydroxypropyl cellulose is present in an amount of 5.0 to 10.0% by weight with respect to the total amount of the pharmaceutical composition.

7. The pharmaceutical composition according to claim 2, wherein magnesium stearate is present in an amount of 1.0 to 3.0% by weight with respect to the total amount of the pharmaceutical composition.

8. The pharmaceutical composition according to claim 6, wherein magnesium stearate is present in an amount of 1.0 to 3.0% by weight with respect to the total amount of the pharmaceutical composition.

9. The pharmaceutical composition according to claim 2, wherein lactose is present in an amount of 44.0 to 87.0% by weight with respect to the total amount of the pharmaceutical composition.

10. The pharmaceutical composition according to claim 2, wherein the low-substituted hydroxypropyl cellulose is present in an amount of 10.0 to 20.0% by weight with respect to the total amount of the pharmaceutical composition.

11. The pharmaceutical composition according to claim 10, wherein magnesium stearate is present in an amount of 1.0 to 3.0% by weight with respect to the total amount of the pharmaceutical composition.

12. The pharmaceutical composition according to claim 11, wherein hydroxypropyl cellulose is present in an amount of 5.0 to 10.0% by weight with respect to the total amount of the pharmaceutical composition.

13. The pharmaceutical composition according to claim 12, wherein lactose is present in an amount of 44.0 to 84.0% by weight with respect to the total amount of the pharmaceutical composition.

14. The pharmaceutical composition according to claim 2, wherein the low-substituted hydroxypropyl cellulose is present in an amount of 10.0% by weight, magnesium stearate is present in an amount of 1.0% by weight and hydroxypropyl cellulose is present in an amount of 5.0% by weight, with respect to the total amount of the pharmaceutical composition.

15. The pharmaceutical composition according to claim 2, wherein the low-substituted hydroxypropyl cellulose is present in an amount of 20.0% by weight, magnesium stearate is present in an amount of 1.0% by weight and hydroxypropyl cellulose is present in an amount of 5.0% by weight, with respect to the total amount of the pharmaceutical composition.

\* \* \* \* \*